United States Patent
Watanabe

Patent Number: 5,554,253
Date of Patent: Sep. 10, 1996

[54] TUBE RESTORING APPARATUS AND TUBE RESTORING METHOD

[75] Inventor: Takahiko Watanabe, Shizuoka-ken, Japan

[73] Assignee: Terumo Kabushiki Kaisha, Tokyo, Japan

[21] Appl. No.: 215,821

[22] Filed: Mar. 22, 1994

[30] Foreign Application Priority Data

Apr. 2, 1993 [JP] Japan .................................. 5-100542

[51] Int. Cl.$^6$ .................................................. B29C 73/00
[52] U.S. Cl. ................ 156/503; 156/304.2; 156/344; 156/581; 156/584; 100/172; 100/232; 128/912; 604/905
[58] Field of Search ..................... 156/344, 584, 156/581, 228, 304.2, 503; 128/912; 241/261.1; 604/905; 100/232, 172; 53/291, 381.1

[56] References Cited

U.S. PATENT DOCUMENTS

| | | | |
|---|---|---|---|
| 2,086,992 | 7/1937 | Weber | 100/232 X |
| 2,379,357 | 6/1945 | Humphrey | 156/581 X |
| 2,780,284 | 2/1957 | Wisti | 156/584 |
| 2,844,184 | 7/1958 | Vollmer | 100/172 |
| 4,261,790 | 4/1981 | Brinker et al. | 156/584 |
| 4,369,779 | 1/1983 | Spencer | 128/213 A |
| 4,475,449 | 10/1984 | Gianelo | 100/232 X |
| 4,677,839 | 7/1987 | Retallick | 100/232 X |
| 4,709,538 | 12/1987 | Olsen, Jr. et al. | 53/381.1 X |
| 4,753,697 | 6/1988 | Shaposka et al. | 156/304.2 X |
| 4,793,880 | 12/1988 | Shaposka et al. | 156/158 |
| 5,039,022 | 8/1991 | Nilsson | 241/261.1 |
| 5,211,109 | 5/1993 | Determan | 100/172 X |

*Primary Examiner*—Mark A. Osele
*Attorney, Agent, or Firm*—Burns, Doane, Swecker & Mathis, LLP

[57] ABSTRACT

A tube restoring apparatus includes a tube insertion passage through which a connected flexible tube having a deformed cross-sectional portion at a joint portion thereof can be passed, at least a pair of press members defining at least a part of the tube insertion passage and formed with press surfaces for pinching the deformed cross-sectional portion of the flexible tube therebetween, and driving mechanism for moving the press surfaces at least in opposite directions relative to each other under the condition that the deformed cross-sectional portion is pressed between the press surfaces. In the apparatus, the deformed cross-sectional portion of which inner surface is fused or stuck by a tube connecting device is disposed between the press surfaces of the press members, and then the press members are moved by the driving mechanism so as to press or roll back and forth the deformed portion of the tube to tear off or separate the fused or stuck portion between the press surfaces, thereby restoring the deformed portion to ensure fluid communication within the tube.

4 Claims, 12 Drawing Sheets

TUBE RESTORING APPARATUS AND TUBE RESTORING METHOD

BACKGROUND OF THE INVENTION

1. Field of the Invention

The present invention relates to tube restoring apparatus and method for restoring a flexible tube used for a liquid transfusing system or a blood transfusing system, or the like, and more particularly to tube restoring apparatus and method for restoring a deformed joint portion of flexible tubes of which inner surface is fused or stuck by fusion, to ensure fluid communication within the connected tube.

2. Description of the Prior Art

Conventionally, as tubes for connecting bags of a liquid transfusing system or a blood transfusing system, polyvinyl chloride tubes are mainly used. Since the polyvinyl chloride tube is formed of a thermoplastic resin, there has been developed sterile tube connecting device (SCD) and connecting method by the device which can connect cut-off tubes under the sterilized condition by utilization of the thermoplastic characteristics of the tubes (which are disclosed in for example U.S. Pat. No. 4,369,779). With this result, it has become possible to cut off and further connect tubes used in a system in which a plurality of bags are connected through the tubes, under the sterilized condition.

The above-mentioned sterile tube connecting device is composed of a cutting blade heated to such a temperature that the tube material can be melted, and two holding members for holding two tubes to be connected. For connection of the tubes, two tubes which are held horizontally and parallel with each other by the two holding members are cut off simultaneously with the heated blade. Further, under the condition that the cut-off surfaces of the tubes are in contact with the heated blade, the holding members are moved so that the cut-off surfaces of the two tubes can be brought into contact with each other, and then the blade is pulled out. However, when the blade is pulled out from between the two cut-off tubes, the cross-sectional shape of the connected tube is usually deformed, so that the tube (polyvinyl chloride) is hardened in the state where the cross-sectional shape of the tube is crushed. In other words, the cross-sectional shape of the tube is usually crushed at the respective joint portion, since the inner surface of the tube at the joint portion is fused or stuck by fusion, so that there is possibility that the tube is closed at the joint portion.

When the tube is crushed at the joint portion thereof after the tubes have been connected to each other, liquid or blood cannot flow therethrough. Therefore, in such a case, it becomes necessary to restore the shape of the deformed joint portion by applying external force to the stuck portion (fused portion) from the outside so as to tear or separate the fused portion formed inside the tube.

Conventionally, the above-mentioned tube restoring operation has been performed by manual operation after the two tubes have been connected to each other. Namely, the joint portion of the tube including the fused portion therein is pinched between the thumb and the index finger of the operator and then rolled therebetween, to separate or tear the fused portion of the tube.

However, since the connected tube is still heated immediately after the two tubes have been connected, there is a danger that the operator may be burnt. In other words, as far as the connected tube is to be restored in shape manually, it is necessary to wait for a certain time until the connected tube is cooled. Therefore, the tube restoring operation cannot be performed immediately after the tube connection process is taken place, thus leading to a problem in that the tube connection process cannot be so far automatized.

SUMMARY OF THE INVENTION

The object of the present invention is to provide a tube restoring apparatus which can restore a tube whose inner surface has been stuck by fusion upon tube connection made by a sterile tube connecting device easily and rapidly without manual operation.

In order to achieve the above mentioned object, a tube restoring apparatus according to the present invention comprises a tube insertion space through which a flexible tube having a deformed cross-sectional portion thereof can be passed, at least a pair of press members defining at least a part of said tube insertion space and formed with press surfaces, respectively, for pinching the deformed cross-sectional portion of the flexible tube therebetween, and driving means for moving at least one of said press surfaces in such a manner that the deformed cross-sectional portion of the flexible tube between said press surfaces is restored.

As described above, when flexible tubes are connected thermally by a sterile tube connecting device, for instance, inner surfaces of the connected tube at the respective joint portions are likely to be fused or stuck by fusion and therefore the joint portion is deformed. As a result, there is a case that the connected tube is closed to such an extent that liquid cannot pass therethrough. Further, even if not closed, the inner cross-sectional area at the joint portion of the tube is reduced by fusion, thus leading to a problem in that it is impossible to obtain a sufficient flow rate. In the tube restoring device according to the present invention, the internally fused portion of the tube or the deformed portion of the connected tube is put in the tube insertion space or passage. Thereafter, a pair of the press members are moved to pinch the tube deformed portion between the press surfaces of the respective press members, so that it is possible to restore the tube so as to tear off or separate the fused portion of the tube, thus enabling to ensure fluid communication through the connected tube.

As stated in the above, in the tube restoring apparatus according to the present invention, it is possible to restore the tube deformation easily and quickly. In particular, since the tube deformation can be restored without manual operation, there is such an advantage that the tube deformed portion can be immediately restored soon after the tubes have been connected.

In one alternative of the tube restoring apparatus according to the present invention, there is provided a pair of press rollers as the press members arranged through a predetermined space therebetween. According to this alternative, the deformed portion of the tube is put between circumferential surfaces of the rollers, and the rollers are rotated through a certain angle to press or squeeze the deformed portion of the tube, whereby tearing or separating the fused portion at the inside of the deformed portion. In this case, it is preferable to form an uneven portion on the respective circumferential surfaces. When the inner fused portion is separated, the inner cross-sectional area of the deformed portion of the tube is restored to the roughly original shape due to its restoring force. If doing so, it is possible to restore the tube without any slip of the tube with respect to the press surfaces. Further, it is also preferable to form a notch on at least one of the rollers which defines the tube insertion passage.

Further, in another alternative of the tube restoring apparatus according to the present invention, there is provided a pair of press members which have opposing press surfaces for pinching the deformed portion of the tube therebetween, in which at least one of the press members is adapted to move at least toward opposite direction relative to the other in parallel to each other. In this alternative, if the press members are moved in relatively opposite directions under the condition that the tube is kept to be pinched between the press surfaces, the tube inner surface is deformed so as to be rubbed with each other in accordance with the movement of the press members, so that it is possible to tear off or separate the fused portion formed at the inside of the deformed portion of the tube. In this case, it is also preferable to form an uneven portion on the respective press surfaces.

Furthermore, in another alternative of the tube restoring apparatus according to the present invention, there is provided at least a pair of press members having opposing press surfaces which can be moved so as to approach to each other. In this alternative, if the tube of which joint portion has been deformed into a flattened shape is pressed from the longitudinal direction thereof by the two opposing press surfaces, it is possible to deform the joint portion into a direction by which the fused portion can be separated or torn off.

In these alternatives, if the moving speeds of a pair of the press members are determined so as to be substantially the same with each other, the tube position will not change during the movement of the press members. This means that, when such a restoring operation is automated, it becomes possible to facilitate the tube positioning operation and other operations subsequent thereto.

Further, when the tube restoring apparatus is linked with a tube connecting device, the joint portion of the connected tubes which has been closed by fusion can be easily restored to enable fluid communication therethrough. In addition, when notches which define the tube insertion space or passage are formed on the press surfaces, it is possible to set the tube to the tube restoring apparatus more easily. These modifications would be useful when the tube restoring apparatus is automated.

In addition, the present invention also provides a tube restoring method of automatically restoring a deformed joint portion which is formed between flexible tubes connected by fusion and of which inner surface is fused or stuck by fusion so as to ensure internal fluid communication of the connected tubes. The method comprises the steps of: positioning the connected tubes at a tube insertion space in such a manner that the joint portion is placed at the tube insertion space or passage; driving at least a pair of press members each having press surfaces, respectively which are adapted to pinch the joint portion therebetween and define at least a part of said tube insertion space or passage; and squeezing or pressing the joint portion by means of said press surfaces so as to tear off or separate the fused portion at the deformed joint portion, whereby restoring the deformed joint portion to ensure the fluid communication within the connected tube.

In one alternative of the tube restoring method according to this invention, said at least a pair of press members are composed of a pair of rollers each having a circumferential surface served as said press surface, and the joint portion of the connected tube is adapted to be pressed and rolled back and forth between said circumferential surfaces of said rollers according to the relative rotational movements of said rollers.

Further, in another alternative of the tube restoring method according to this invention, said at least a pair of press members include a pair of opposing surfaces served as said press surfaces, and the joint portion of the connected tube is adapted to be pressed and rolled back and forth between said opposing surfaces according to the relative parallel movements of said press members.

Further, in yet another alternative of this invention, said at least a pair of press members include a pair of opposing surfaces served as said press surfaces, and the joint portion of the connected tubes which has been deformed into a flattened shape is adapted to be pressed from both sides of the longitudinal direction of the flattened shape between said opposing surfaces according to the movements of said press members in their approaching direction.

Other objects, features and advantages of the present invention will be apparent when the following detailed description of the preferred embodiments is considered in conjunction with the attached drawings.

BRIEF DESCRIPTION OF THE DRAWINGS

FIGS. 6A to 6E are entire front views for assistance in explaining tube restoring processes by a third embodiment of the tube restoring apparatus according to the present invention, in which FIG. 6A shows the condition that the tube is pinched into a flattened shape between the press surfaces; FIG. 6B shows the condition that the flatly deformed tube is being rolled so as to be perpendicular to the press surfaces; FIG. 6C shows the condition that the flatly deformed tube has been set perpendicular to the press surfaces; FIG. 6D shows the condition that pressure is being applied to the flatly deformed tube by narrowing the space between the press members to tear off or separate the inner fused portion; and FIG. 6E shows the condition that the space between the press members is further narrowed to crush the tube perfectly.

FIGS. 7A to 7E are partial front views showing the structure of a fourth embodiment of the tube restoring apparatus according to the present invention and the tube restoring processes by this embodiment, in which FIG. 7A shows the arrangement of the press surfaces of the press members; FIG. 7B shows the flatly deformed tube is crushed between a first pair of the press members in a direction that a second pair of the press members are arranged; FIG. 7C shows the condition that the tube is pressed and deformed by the second pair of the press members to tear off or separate the fused inner portion thereof; FIG. 7D shows the condition that the tube is perfectly crushed; and FIG. 7E shows the condition that the cross-sectional shape of the tube is perfectly restored to the original shape.

FIGS. 8A to 8C are partial front views showing the structure of a fifth embodiment of the tube restoring apparatus according to the present invention and the tube restoring processes by this embodiment, in which FIG. 8A shows the arrangement of the press surfaces of the press members in which the tube is rotated by 90 degrees from the position shown in FIG. 7B so that the longitudinal direction of the flattened tube is set to the press direction of the press members; FIG. 8B shows the condition that the tube is crushed by the press members; and FIG. 8C shows the condition that the press members are retracted and the cross-sectional shape of the tube is restored to the roughly original shape.

DETAILED DESCRIPTION OF THE PREFERRED EMBODIMENTS

Figure 1:
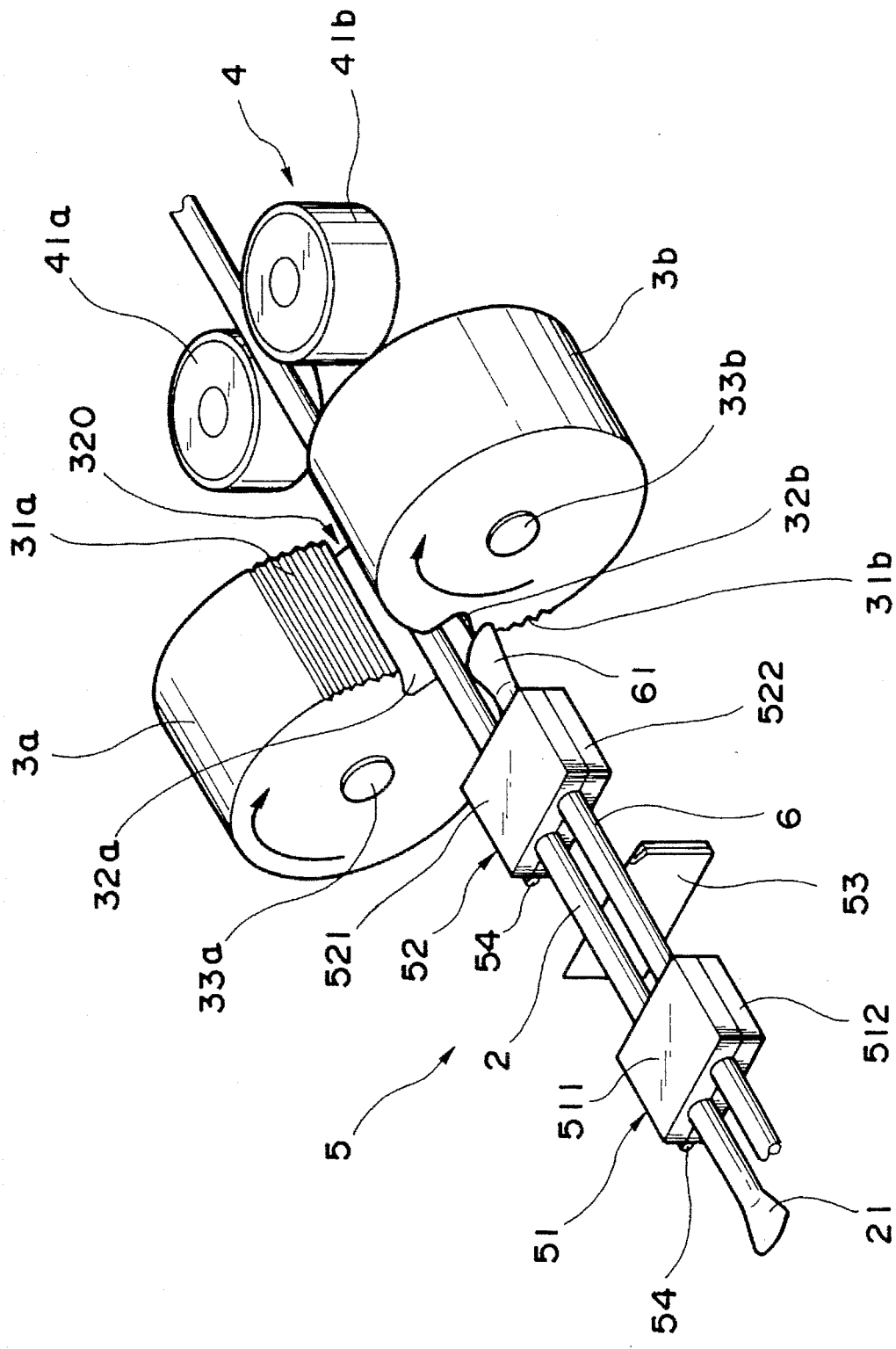
FIG. 1 is an entire perspective view showing a first embodiment of the tube restoring apparatus according to the present invention.
Figure 2A:
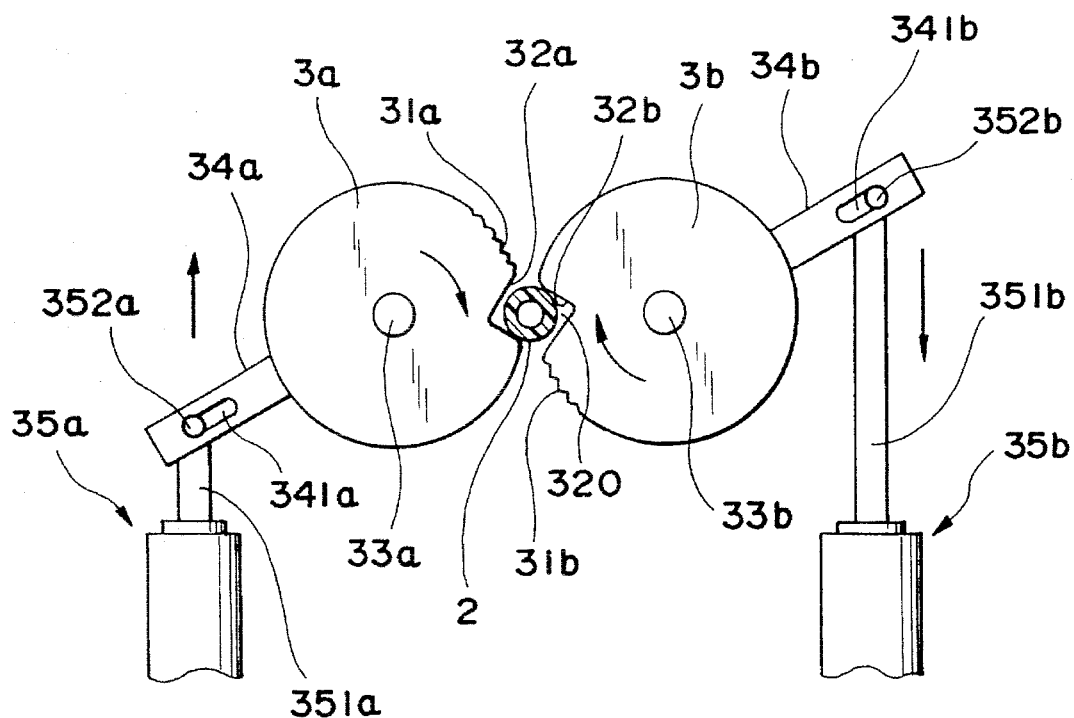
FIG. 2A is an entire front view of the first embodiment showing the condition that a tube insertion passage is formed in the apparatus.
Figure 2B:
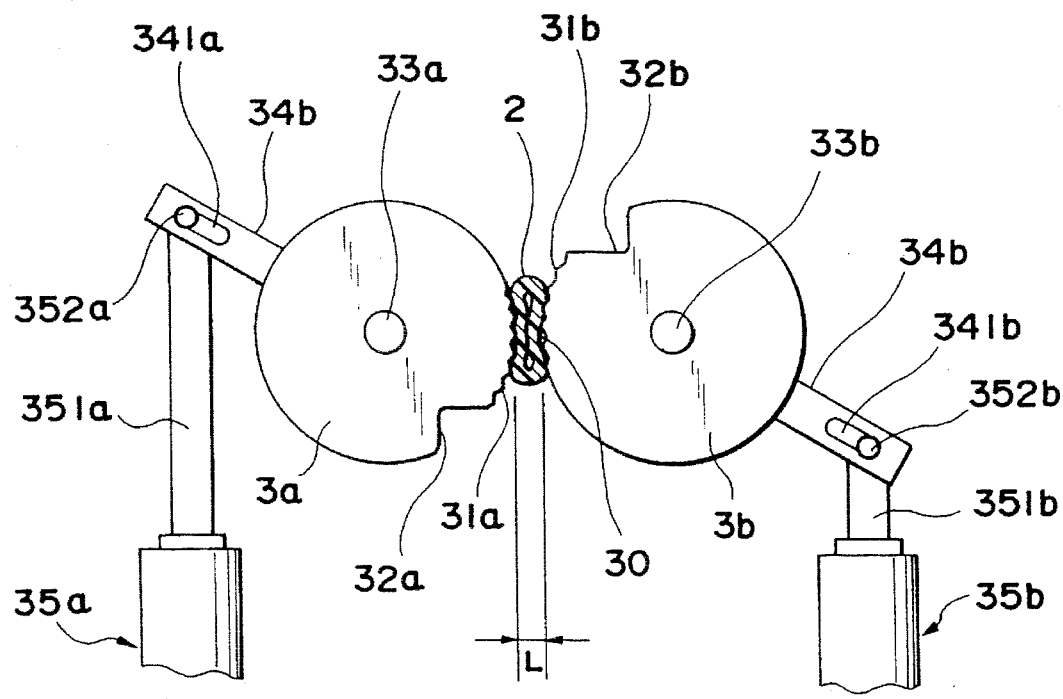
FIG. 2B is an entire front view of the first embodiment showing the condition that the tube is being restored by the apparatus.

The preferred embodiments of the present invention will be described hereinbelow with reference to the attached drawings. FIG. 1 is an entire perspective view showing the tube restoring apparatus according to the present invention; and FIGS. 2A and 2B are front views showing the tube restoring apparatus shown in FIG. 1. The tube restoring apparatus is composed of a pair of press rollers 3a and 3b for pressing a tube 2, which serve as the pressing members; pivotal arms 34a and 34b; and reciprocating motion mechanisms 35a and 35b for rotating the press rollers 3a and 3b via the pivotal arms 34a and 34b, which serve as the driving means.

The press rollers 3a and 3b are cylindrical in shape, and pivotally supported at two mutually parallel positions by two parallel supported pivotal axes 33a and 33b, respectively. A gap is formed between the two pivotally supported press rollers 3a and 3b as a tube insertion space 30 through which the tube 2 is inserted and passed, as shown in FIG. 2B.

On each of the outer circumferential surfaces of the press rollers 3a and 3b, a groove-shaped cutout portion or notch 32a and 32b is formed so as to extend in the axial direction thereof, respectively. As shown in FIG. 2, when the press rollers 3a and 3b are rotated in the same (clockwise, in FIG. 2) direction to such a position at which the respective cutout portions or notches 32a and 32b are opposed to each other, it is possible to form the tube insertion passage 320 (through which the tube 2 can be passed) with the two cutout portions 32a and 32b of the press rollers 3a and 3b. The dimension of the tube insertion passage 320 is large to such an extent that the tube 2 of the ordinary cross-sectional shape can be passed freely therethrough.

On the circumferential surfaces of the press rollers 3a and 3b, two press surfaces 31a and 31b each having an uneven or a rough configuration are formed on one side of and in the vicinity of the cutout portions 32a and 32b, respectively. These press surfaces 31a and 31b are curved surfaces having the same radius of curvature as that of the circumferential surfaces of the press rollers 3a and 3b, respectively. Further, as illustrated in FIG. 2B, each of the press surfaces 31a and 31b is so arranged on each press roller 3a and 3b as to be opposed to each other at the time when the respective press rollers 3a and 3b are rotated in the same direction (clockwise) from the position at which the tube insertion passage 320 can be formed. Under the condition that the two press surfaces 31a and 31b face each other, a distance L of a gap 30 between the two press surfaces 31a and 31b is smaller than an addition of two wall thicknesses of the tube 2 passing therethrough (which corresponds to a difference between the outer and inner diameters) (referred to as "α"), preferably about 95 to 50% of "α", and more preferably about 90 to 70% of "α".

The pivotal arms 34a and 34b are fixed to the press rollers 3a and 3b in such a way as to project from the press rollers 3a and 3b in the radial direction thereof, respectively. The pivotal arms 34a and 34b are formed with slots 341a and 341b on the outer ends thereof in such a way that the longitudinal direction of the slots extends through the radial direction of the press rollers, respectively. In a case where the press rollers 3a and 3b are rotated about and together with the pivotal axes 33a and 33b, respectively, it is possible to fix the pivotal arms 34a and 34b directly to the pivotal axes 33a and 33b, respectively, instead of fixing the pivotal arms 34a and 34b to the press rollers 3a and 3b.

On the extension lines along which the ends of the pivotal arms 34a and 34b are moved, two reciprocating motion mechanisms 35a and 35b are disposed, respectively. In this embodiment, pneumatic actuators are used as the reciprocating motion mechanisms 34a and 35b, respectively. On one ends of drive rods 351a and 351b of the pneumatic actuators, pins 352a and 352b are provided, respectively so as to be engaged with the slots 341a and 341b of the pivotal arms 34a and 34b, respectively.

Therefore, when the drive rods 351a and 351b are moved upwardly and downwardly, the pivotal arms 34a and 34b are pivoted, because the pins 352a and 352b are moved along the longitudinal direction of the slots 341a and 341b, respectively.

Without being limited to only the pneumatic actuators, any displacement mechanisms such as hydraulic actuators, cam mechanisms, electric driving mechanisms, etc. can be used for the reciprocating motion mechanism 35a and 35b. Further, as means for driving the press rollers 3a and 3b, it is also possible to use a motor linked with the pivotal axes 33a and 33b, without being limited to only the combination of the pivotal arms 34a and 34b and the reciprocating motion mechanisms 35a and 35b.

As shown in FIG. 1, a tube feed mechanism 4 is provided on the extension line of the tube insertion passage 320. The tube feed mechanism 4 is composed of two feed rollers 41a and 41b. The positions of the two feed rollers 41a and 41b are such that a space between the circumferential surfaces of the feed rollers 41a and 41b is slightly smaller than the diameter of the tube. Therefore, when the tube 2 is pinched between the two feed rollers 41a and 41b and then the respective feed rollers 41a and 41b are rotated in the mutually opposite directions, it is possible to feed the tube 2 in the axial direction thereof. Owing to the feed mechanism 4, the tube 2 can be fed into the tube insertion passage 320 and can be extracted from the tube insertion passage 320.

As a material for the tube 2 to be inserted into the tube insertion passage 320 of the tube restoring apparatus, it is possible to selectively use one or more of various materials including polyvinyl chloride; polyolefin such as polyethylene, polypropylene, EVA; polyester such as PET or PBT; polyurethane; polyamide; silicone; or thermoplastic elastomer such as polyester elastomer, polyamide elastomer, styrene-butadiene copolymer. Among these materials, the polyvinyl chloride is particularly preferable as the material of the tube 2.

Further, although not specified, the inner diameter of the tube 2 is usually 2 to 15 mm, and more preferably 2 to 5 mm.

The tube 2 is usually connected to a blood collecting bag, a liquid transfusing vessel (in which liquid flowing through the tube is accommodated), an empty vessel (in which liquid to be transfused is not yet put), etc. However, a simple tube which is not connected to another bag or vessel can also be used as the tube.

On the other hand, a tube connecting device 5 is disposed on the side of the tube restoring apparatus 1 remote from the tube feed mechanism 4, as shown in FIG. 1.

Figure 3:
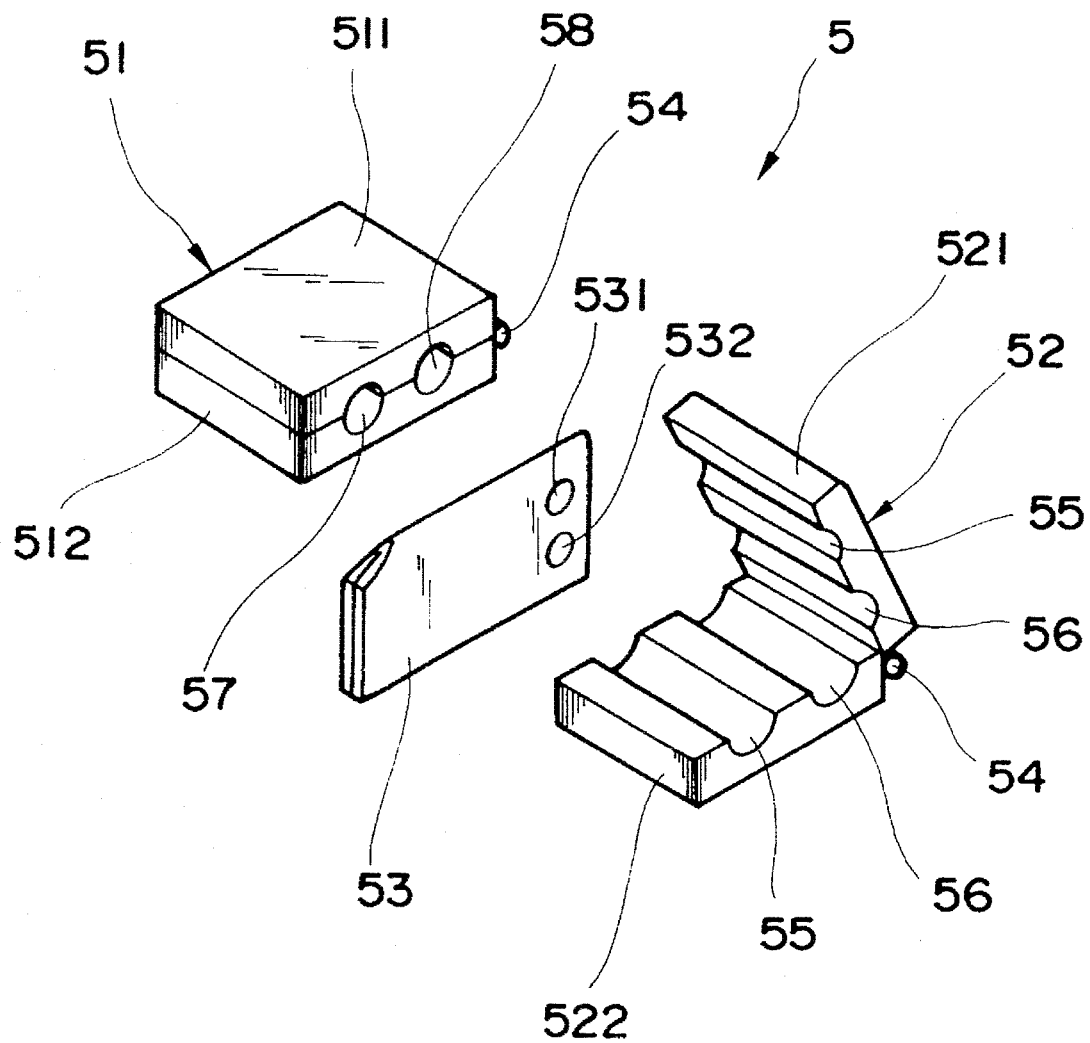
FIG. 3 is a perspective view showing the structure of the essential portion of the tube connecting device.

FIG. 3 is a perspective view showing the structure of the essential portion of the tube connecting device 5, and FIGS. 4A to 4D are perspective views for assistance in explaining the connecting process of the tubes 2 and 6 by the tube connecting device 5. As shown in these drawings, the structure of the tube connecting device 5 includes a pair of holders 51 and 52, and a wafer (a plate-shaped heating element) replaceably interposed between the holders 51 and 52. In the tube connection, ends of the two tubes 2 and 6 are arranged between the holders 51 and 52; the arranged tubes are melted and cut off by the heated wafer 53; one of the holders 51 is shifted; and the wafer 53 is removed; and thus the tubes 2 and 6 can be connected by fusion.

In more detail, the holders 51 and 52 are composed of two holder pieces 511, 512 and 521, 522 respectively, as shown in FIG. 3. These holder pieces 511, 512 and 521, 522 are pivotal about a hinge 54, respectively.

Further, two semi-circular (in cross section) grooves are formed on two opposing inner surfaces of the respective holder pieces 511, 512 and 521, 522, respectively in such a way that two circular tube holding portions 57 and 58 can be defined when the holder pieces 511, 512 and 521, 522 are folded over each other.

Further, although not shown, tube pinching portions may be formed on the ends of the holders 51 and 52 and on the side of the wafer 53 so that the inner surfaces of the tubes 2 and 6 can be pressed in such a manner that the inner spaces thereof are closed, respectively, when the holder pieces 511, 512 and 521, 522 are folded.

The wafer 53 is formed by folding a metallic (e.g., copper) plate in two and by arranging any desired pattern of heating resistance (not shown) through two insulating layers disposed between the respective inner surface of the metallic plate and the respective outer surface of the heating resistance, respectively. Both terminals 531 and 532 of the heating resistance are taken out through two holes formed in one of the metallic plates, respectively. Further, it is preferable to use this wafer 53 only once and then to throw it away (single use) whenever the tube is connected.

The method of connecting tube by the tube connecting device as described above will be described hereinbelow.

Figure 4A:
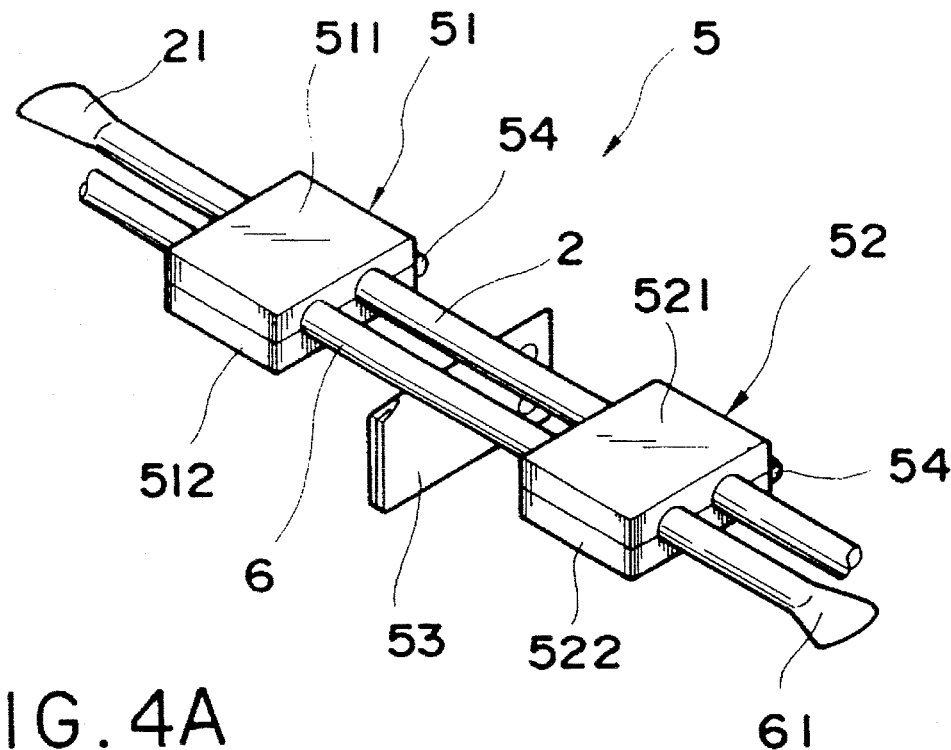
FIGS. 4A to 4D are perspective views for assistance in explaining the tube connection process effected by the tube connecting device shown in FIG. 3.

As shown in FIG. 4A, the ends of the tubes 2 and 6 are previously sealed by a tube sealer (not shown) so as to form closure ends 21 and 61, respectively. Two tubes 2 and 6 of a constant length are arranged in parallel to each other in the grooves 55 and 56 of the two holders 51 and 52 in such a way that the closure ends 21 and 61 of the tubes are directed toward two opposite directions, respectively. Then, the holder pieces 511, 512 and 521, 522 are closed to pinch and fix the two tubes 2 and 6 between the tube holder portions 57 and 58, respectively.

Thereafter, a voltage (e.g., 6 to 24 V) is applied across the terminals 531 and 532 by current supplying means to pass current through the heating resistance of the wafer 53. Therefore, the heating resistance is heated and thereby the wafer 53 is heated up to a temperature (e.g., 220° C. to 260° C.) beyond the melting point of the tubes 2 and 6.

Figure 4B:
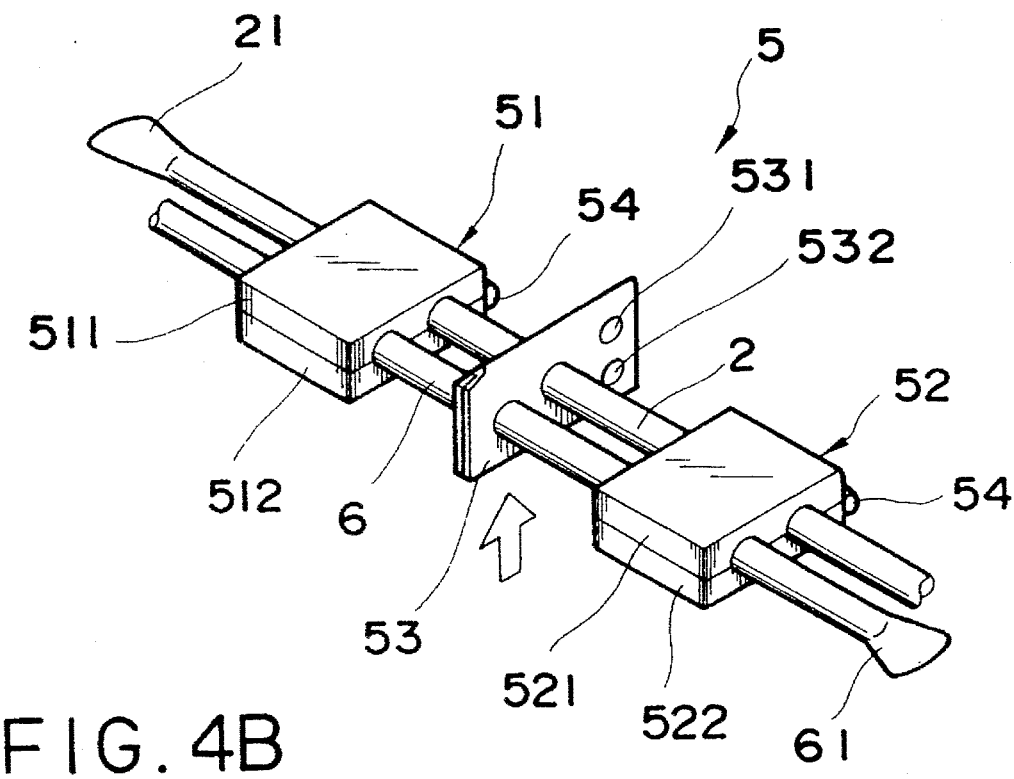

Under these conditions, as shown in FIG. 4B, when the wafer 53 is moved upwardly, the tubes 2 and 6 are melted and cut off by the heat of the wafer 53. Under these conditions, since the cut-off ends of the tubes 2 and 6 are melted and softened as well as kept at a high temperature without being exposed to any external objects, it is possible to maintain a sterile status of both the tubes 2 and 6.

Figure 4C:
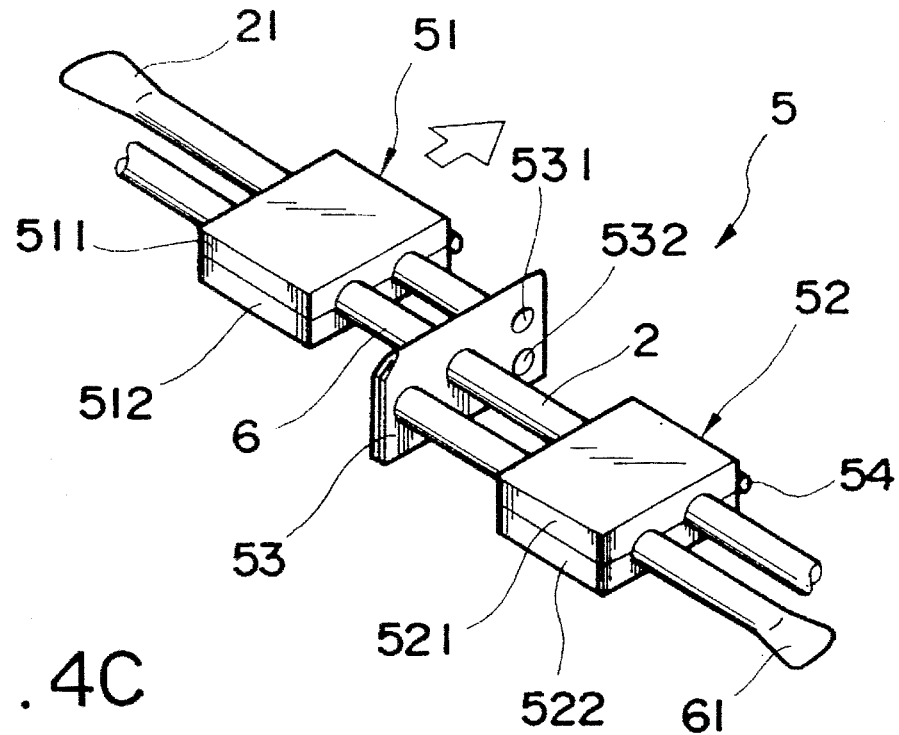

Thereafter, as shown in FIG. 4C, one holder 51 is moved in the tube arrangement direction under the condition that the cut-off ends of the tubes 2 and 6 are kept melted, and then stopped and fixed at such a position that two cut-off ends of the tubes 2 and 6 are arranged so as to be concentric with respect to each other.

Figure 4D:
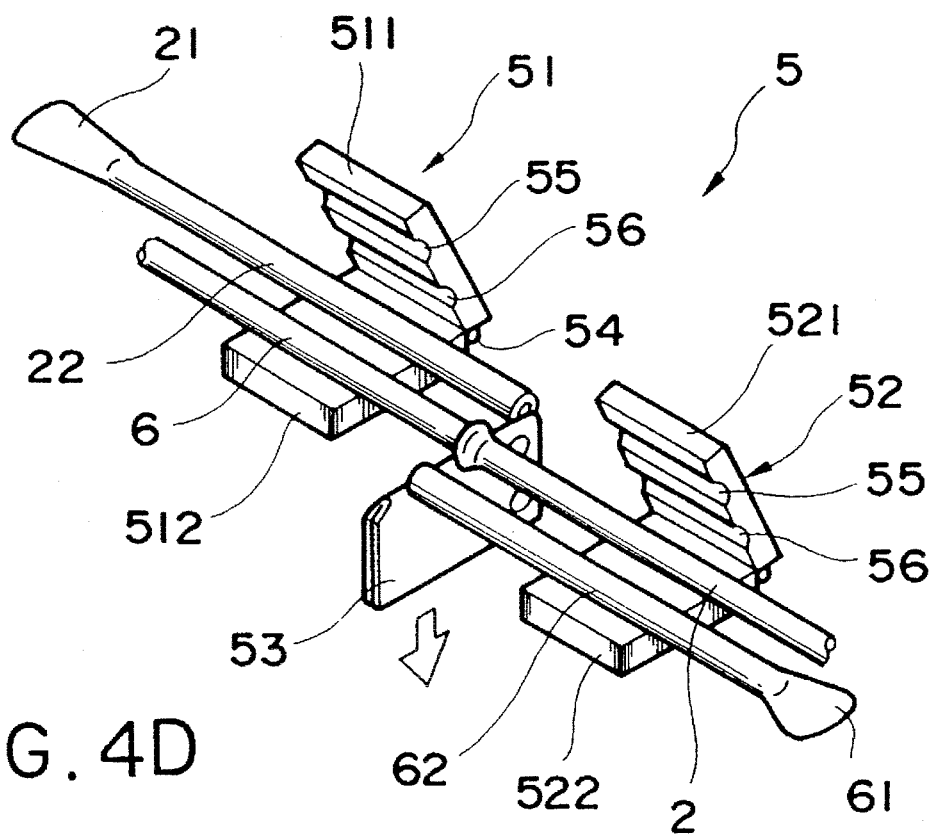

Further, as shown in FIG. 4D, the wafer 53 is extracted downwardly, and one holder 51 is pressed slightly against the other holder 52 to connect the cut-off ends of the two tubes 2 and 6 by fusion.

As described above, in a series of the operation from the cutting-off to the connection of the tubes 2 and 6 with the use of the wafer 53, the cut-off ends and the periphery of the tubes 2 and 6 are kept melted or softened at a relatively high temperature and further in contact with the surfaces of the heated wafer 53 until the cut-off ends are brought into tight contact with each other and further connected by fusion, without being exposed to any outside substance. Therefore, it is possible to retain the inner surfaces of the tubes under almost perfect sterile condition.

After the tubes have been connected, the remaining tubes 22 and 62 including the cut-off closure ends 21 and 61 are removed from the holders 51 and 52, respectively, and then discarded.

Further, when other tubes are connected in the succeeding process, the used wafer 53 is replaced with a new wafer 53, and the used wafer 53 is discarded.

In the above-mentioned process, when the wafer 53 is pulled out or extracted, the inner surfaces of the connected portions of the tubes 2 and 6 are usually stuck to each other by fusion and thereby deformed into a flat shape, with the result that the tubes are likely to be closed. Further, even if not closed, the inner surface of the tube is fused or stuck by fusion partially and thereby the cross-sectional area of the tube is reduced, with the result that a sufficient flow rate of liquid cannot be expected. As described above, the tube having thus formed flat or closed cross-sectional shape; that is, the deformed portion of the tube is restored in shape by the already explained tube restoring apparatus 1 so that the inner passage of the tube can be opened and thereby a sufficient cross-sectional area served as the flowing passage can be obtained.

The function of the tube restoring apparatus according to the present invention will be described hereinbelow with reference to FIG. 2A again. The press rollers 3a and 3b are rotated by the driving means until the cutout portions or notches 32a and 32b face each other so that the tube insertion passage 320 can be defined. Under these conditions, the tube feed mechanism 4 (shown in FIG. 1) is actuated to feed the end of the tube 2 into the tube insertion passage 320 so as to reach the tube connecting device 5 disposed beyond the tube insertion passage 320. The tube 2 fed to the tube connecting device 5 is located in the grooves 55 and 56 formed in the holder pieces 512 and 522, respectively under the conditions that the two holders 51 and 52 are kept opened. Further, the tube 6 to be connected to the tube 2 is located in the grooves 55 and 56 formed in the holder pieces 512 and 522, respectively, thereafter the holder pieces 511 and 512 are both closed. Under these conditions, the tubes 2 and 6 are connected to each other in accordance with the method as already described.

After the tube connection, the holder pieces 511 and 521 are both opened. Therefore, the tube feed mechanism 4 is driven until the connected portion deformed flat due to the connection is located within the tube insertion passage 320.

Further, the reciprocating motion mechanisms 35a and 35b are driven to rotate the press rollers 3a and 3b. As shown in FIG. 2B, when the press rollers 3a and 3b are rotated, the tube is crushed between the two press surfaces 31a and 31b and further twisted in such a way that the inner surface of the crushed portion can be rubbed with each other. When the tube is crushed as described above, the fused or stuck portion at the inner surface thereof can be ripped or separated. In addition, if the tube is further rolled back and forth in such a way that the tube inner surface is rubbed with each other under the crushed condition, it is possible to securely tear off or separate the inner fused portion, with the result that the tube can be restored into the original or roughly original circular cross-sectional shape.

Here, the rotational angle of the press rollers 3a and 3b is set to such a small extent that the tube inner surface having the fused connection can be slightly rubbed with each other. Namely, the fused connection can be sufficiently separated without rotating the press rollers through an excessively large angle. For instance, when the diameter of the press rollers is 10 times larger than that of the tube, the rotational angle of the press rollers required to rotate (twist) the tube through 180 degrees is about 25 degrees.

Finally, the press rollers 3a and 3b are further rotated by the reciprocating motion mechanisms 35a and 35b to the position where the two cutout portions or notches 32a and 32b can be opposed to each other to form the tube insertion passage 320. Further, the tube feed mechanism 4 is driven to pull out the tube from the tube insertion passage 320.

Here, since the press surfaces 31a and 31b of the press rollers 3a and 3b are moved in two mutually opposite directions, the axial line of the tube 2 is kept almost unchanged. Accordingly, it is possible to prevent the axial line of the tube from being dislocated and thereby the tubes 2 and 6 from being dislodged from the tube feed mechanism 4 or the tube connecting device 5, during the restoring operation in the tube restoring apparatus 1. In particular, since the tube moving speeds of both the press surfaces 31a and 31b are substantially the same with each other, the tube axial line is hardly dislocated, and thereby the above described effect can be obtained securely. This effect is extremely advantageous when the tube connecting device is required to be automated.

As described above, it is possible to achieve the two operations which connects tubes and restores the connected tube which has been deformed flat with the mechanical and continuous processes.

Figure 5:
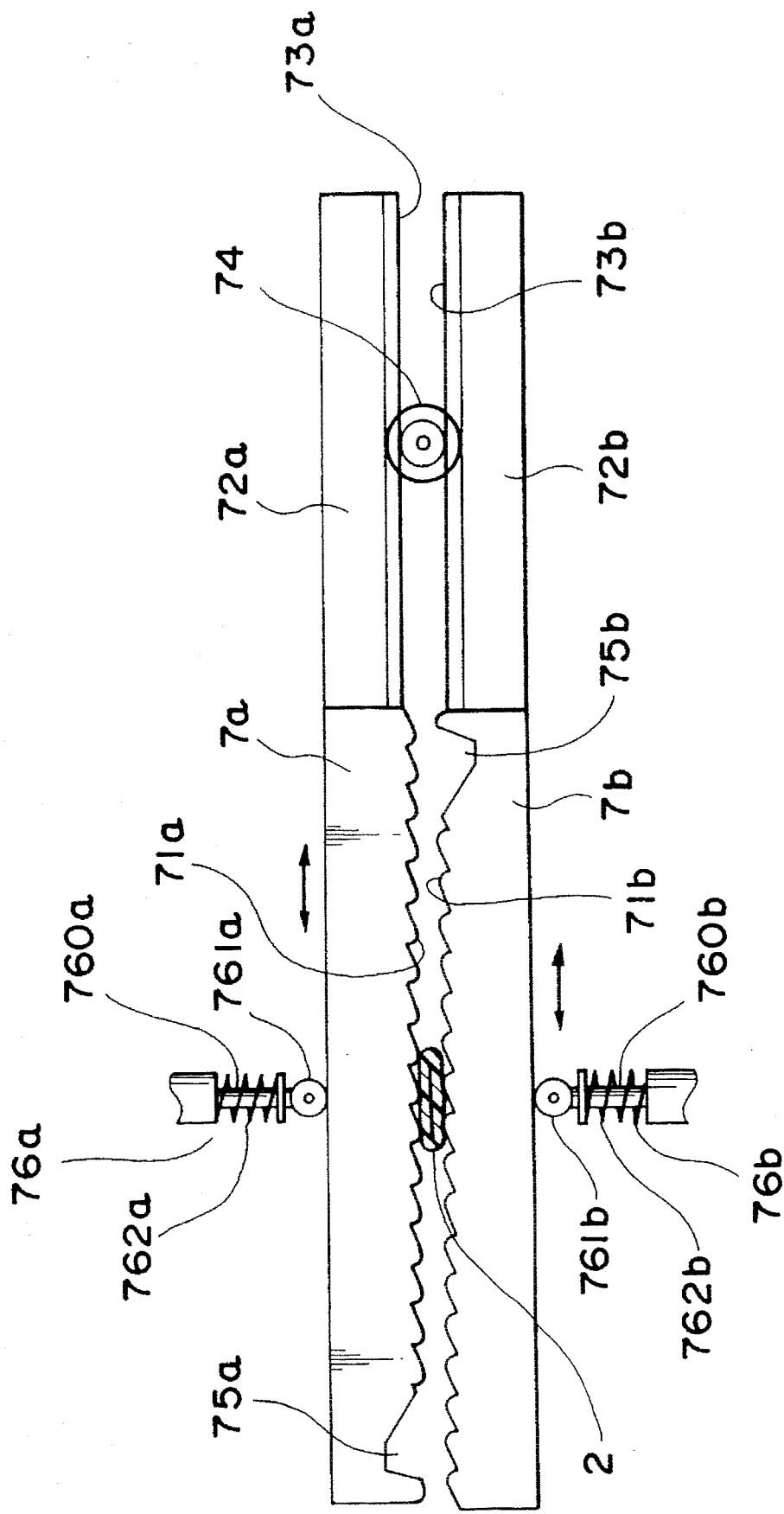
FIG. 5 is an entire front view showing a second embodiment of the tube restoring apparatus according to the present invention.

FIG. 5 shows a second embodiment of the present invention. In this embodiment, the press members 7a and 7b are both formed as plate-like shape having press surfaces 71a and 71b which are opposed to each other, respectively. The two press members 7a and 7b are arranged in parallel to and in the close vicinity of each other in such a way that the two opposing surfaces 71a and 71b can crush the tube 2 by pinching the tube therebetween. Further, the press surfaces 71a and 71b are formed with a rough or an uneven portion, respectively to prevent the tube 2 from sliding on the press surfaces 71a and 71b when the tube 2 is squeezed or twisted between the press surfaces.

On one ends of the press members 7a and 7b, two arms 72a and 72b are arranged, respectively so as to be opposed to each other. The arms 72a and 72b are formed with racks 73a and 73b, respectively. A pinion 74 which is in mesh with the racks 73a and 73b is interposed between the two arms 72a and 72b. Therefore, when this pinion 74 is rotated, it is possible to move the press members 7a and 7b in two mutually opposite directions at substantially the same moving speed.

On the other hand, the surfaces of the press members 7a and 7b remote from the press surfaces 71a and 71b are formed flat, respectively. Further, two urging means 76a and 76b are provided so as to urge the press members 7a and 7b toward each other, respectively in the direction that the tube 2 can be crushed or pinched between the press surfaces. The urging means 76a and 76b are composed of cylinder rods 760a and 760b projecting from two cylinders, respectively; two free rollers 761a and 761b rotatably supported at both ends of the cylinder rods 760a and 760b, respectively; and springs 762a and 762b interposed between the free rollers 761a and 761b and the cylinders, respectively. Accordingly, the press members 7a and 7b are urged by the two springs 762a and 762b, respectively in the directions that the tube can be crushed. When the press members 7a and 7b are moved in parallel to each other, the free rollers 761a and 761b are both rotated and therefore the press members 7a and 7b are always urged by the springs 762a and 762b through the free rollers 761a and 761b, respectively.

Further, two cutout portions or notches 75a and 75b are formed on the press surfaces 71a and 71b on the sides remote from each other, respectively. Accordingly, when the press members 7a and 7b are moved to such positions that the two cutout portions 75a and 75b are opposed to each other, a tube insertion passage is formed by these cutout portions.

In the second embodiment of the tube restoring device as described above, when the two press members 7a and 7b are moved in parallel to each other under the conditions that the tube 2 is crushed between the press surfaces 71a and 71b, the inner surface of the tube 2 can be rubbed with each other or squeezed or twisted in accordance with the movement of the press members 7a and 7b, so that it is possible to separate or tear off the inner fused or stuck portion at the deformed portion of the tube.

FIGS. 6A to 6E show a third embodiment of the present invention, in which press members 9a and 9b similar to those of the second embodiment are used. The press members 9a and 9b are both formed into plate-like shape having press surfaces 91a and 91b, respectively. The two press members 9a and 9b are arranged in parallel to and in the close vicinity of each other in such a way that the two opposing press surfaces 91a and 91b can crush the tube 2. Further, the press surfaces 91a and 91b are formed with a rough surface, respectively to prevent the tube 2 from sliding on the press surfaces 91a and 91b when the tube 2 is squeezed or twisted therebetween.

Figure 6A:
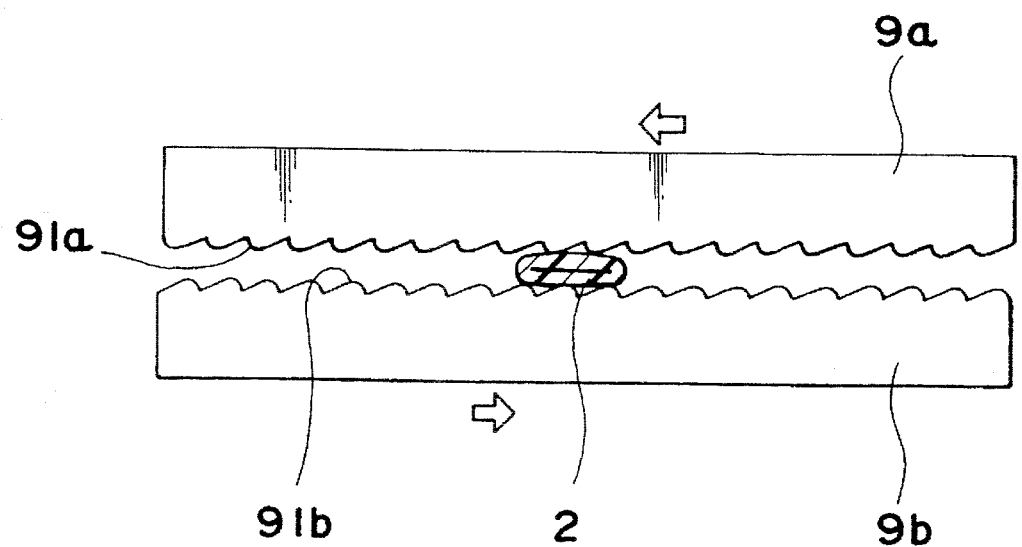
Figure 6B:
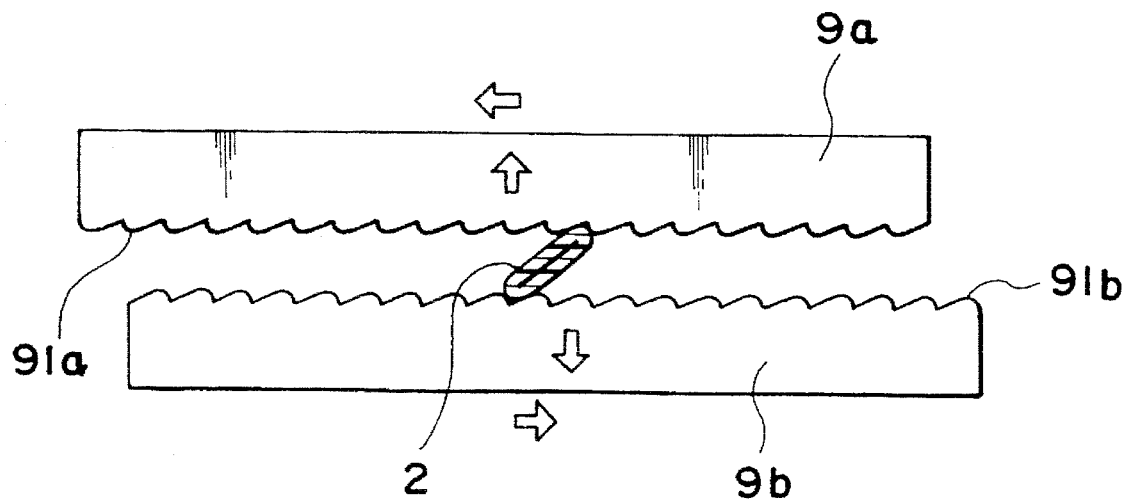

In this embodiment, the two press surfaces 91a and 91b between which the tube 2 is being pinched are moved in two opposite directions parallel to the press surface extending direction as well as in the direction perpendicular thereto. That is, two press surfaces 91a and 91b are moved in the surface direction in parallel to each other while changing the space between the two surfaces gradually. Under the process, when the deformed portion of the tube 2 is pinched between both the press surfaces 91a and 91b (as shown in FIG. 6A), the press members 9a and 9b are once stopped. Further, as shown in FIG. 6B, under the condition that the tube 2 is pinched therebetween, the press members 9a and 9b are moved in parallel to each other as well as in the direction perpendicular thereto, to widen the space between the two press surfaces 91a and 91b gradually. Thereafter, the press members 9a and 9b are stopped at the time when the relative parallel movement distance of the two press surfaces 91a and 91b and the widened space distance between both the press members 9a and 9b become roughly equal to the tube width obtained when the tube is deformed flat, respectively.

Figure 6C:
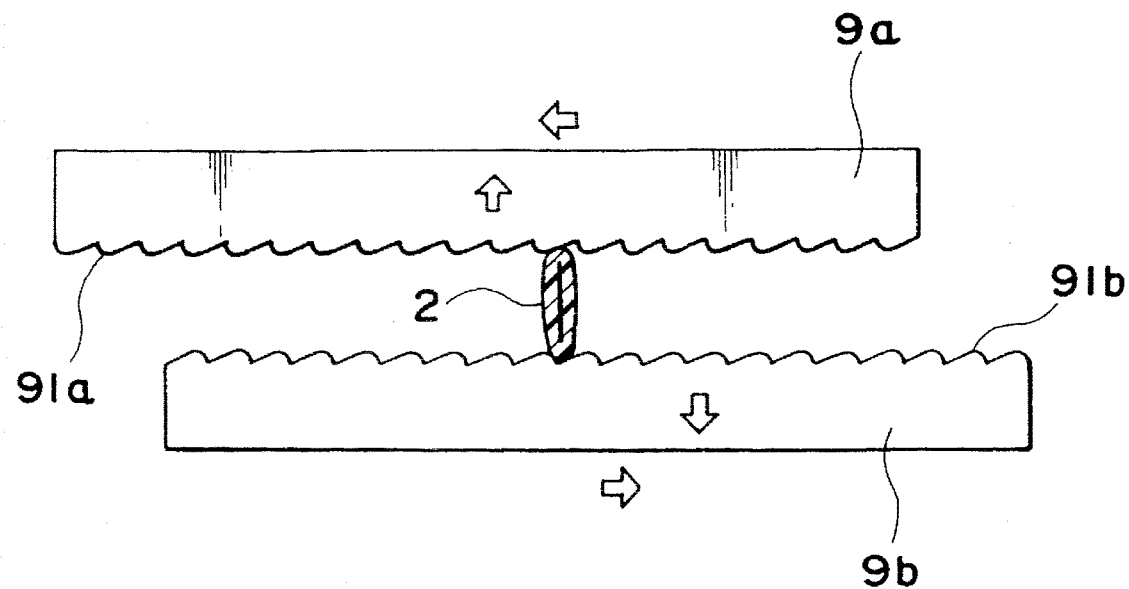
Figure 6D:
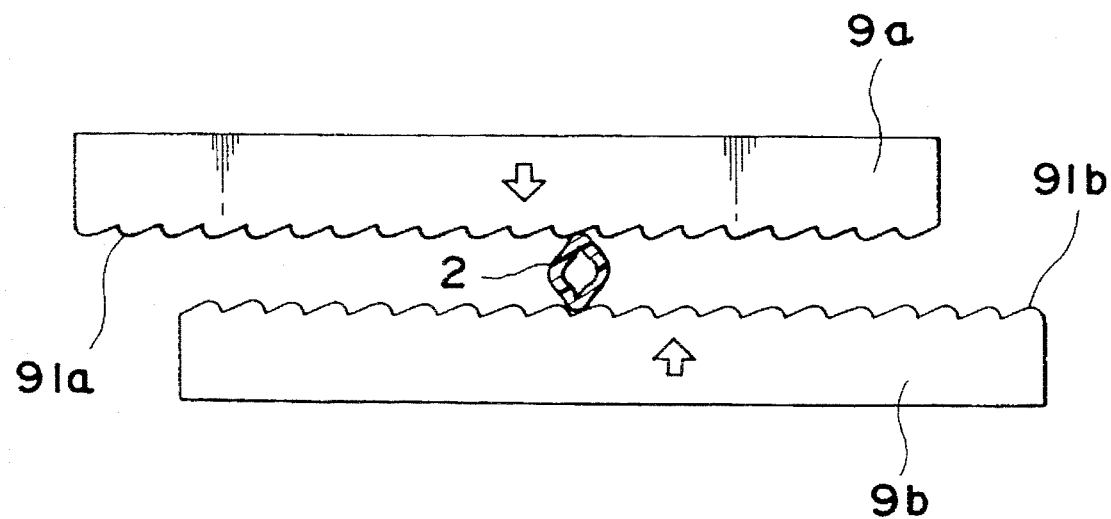
Figure 6E:
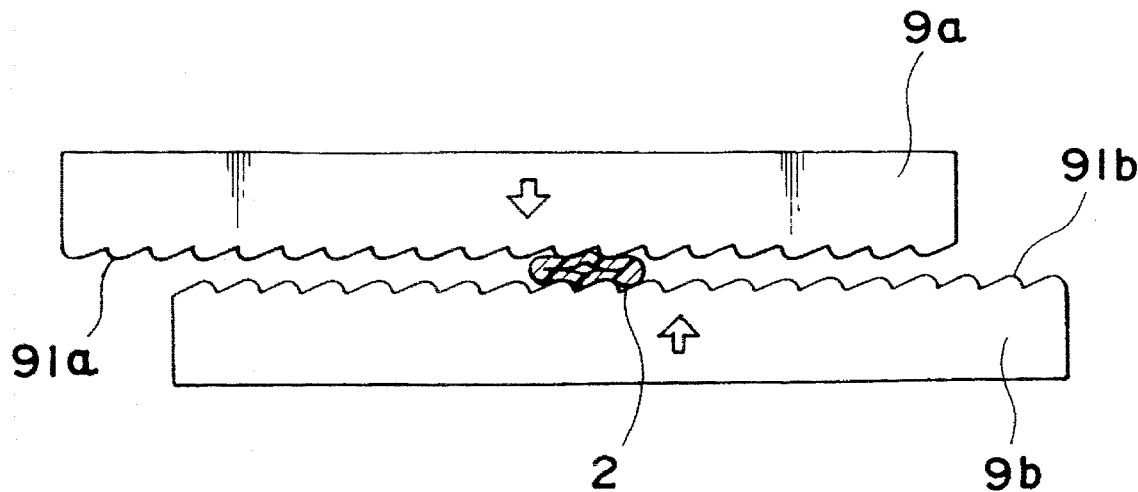

Under these conditions, as shown in FIG. 6C, the tube 2 is held vertically between the rough surfaces of the press surfaces 91a and 91b. In this situation, the space between both the press members 91a and 91b is narrowed to deform the tube in the direction that the fused connection can be separated or torn, as shown in FIG. 6D. To further securely separate the fused connection, as shown in FIG. 6E, the tube 2 is further crushed. Thereafter, the press members 9a and 9b are moved in parallel to each other to the original position. The above-mentioned operation is repeated a few times.

In the above-mentioned third embodiment, an external force is applied to the flatly deformed portion of the tube (at which the inner surface of the tube has a fused connection) from the longitudinal direction thereof to widen the tube deformed portion.

As alternatives in which an external force is applied to the crushed tube as explained above to restore the deformed portion by separating the fused portion, there are the following fourth and fifth embodiments.

Figure 7A:
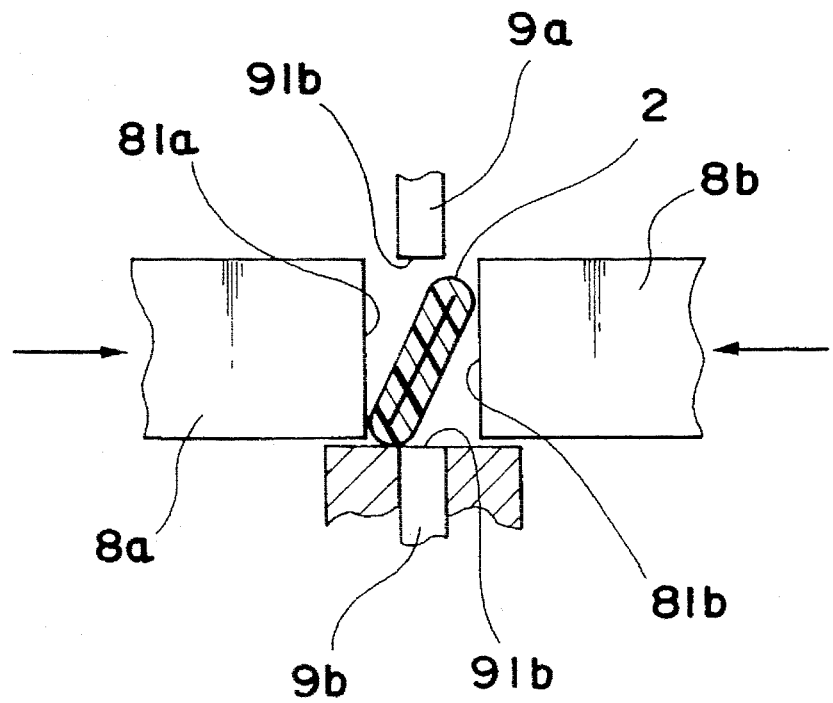

FIG. 7A shows the fourth embodiment of the present invention. In this embodiment, first and second pairs of press members 8a, 8b and 9a, 9b are arranged. These first and second press members 8a, 8b and 9a, 9b are reciprocatingly actuated linearly only in the direction that the tube interposed between the press surfaces can be crushed, respectively. That is, the first press members 8a and 8b are arranged so as to be reciprocatingly moved in the right and left direction in FIG. 7A, and the second press members 9a and 9b are arranged so as to be reciprocatingly moved in the upper and lower direction in FIG. 7A. Further, the respective opposing surfaces 81a, 81b and 91a, 91b of these press members 8a, 8b and 9a, 9b serve as the press surfaces, respectively, by which the tube 2 is crushed.

Under the standby condition, the respective press surfaces 81a, 81b and 91a, 91b are spaced away sufficiently from each other so as to form a tube insertion space into and through which the tube can be inserted and passed. To these press members 8a, 8b and 9a, 9b, the reciprocating motion mechanisms such as pneumatic actuators, for instance are linked, respectively. In this case, ends of cylinder rods are connected to these press members, respectively, so that the two opposing press members can be moved back and forth with keeping parallel relationship with each other in accordance with the reciprocating motion thereof, respectively.

Figure 7B:
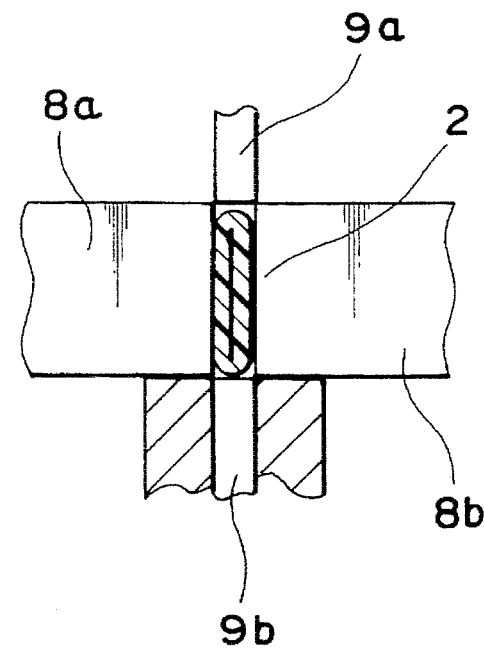

As shown in FIG. 7A, the deformed portion of the tube (whose cross-sectional shape is deformed flat because the inner surface thereof is fused or stuck by fusion) is located in the tube insertion space, and the first press members 8a and 8b are moved in the direction that the two press surfaces 81a and 81b are approached with each other. Then, the deformed portion of the tube located in the tube insertion space is pinched between the two press surfaces 81a and 81b so that the longitudinal direction of the cross section of the flat tube is set perpendicular to the press surfaces 91a and 91b, as shown in FIG. 7B.

Figure 7C:
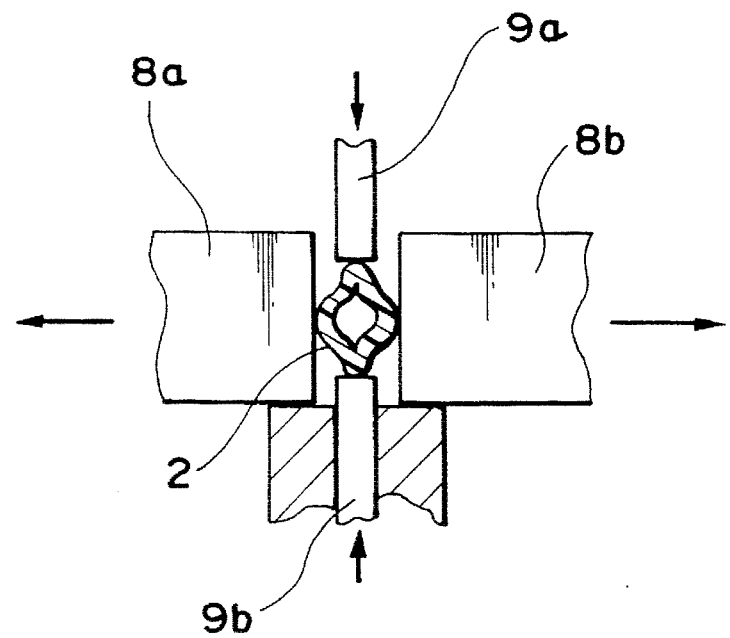

Here, the second press members 9a and 9b are moved in the direction that the space therebetween is to be narrowed. Then, as shown in FIG. 7C, since pressure is applied to the tube and thereby the tube is compressed from the longitudinal directions thereof, the tube 2 is deformed in such a way that the inner fused portion of the tube 2 is separated. In this case, the first press members 8a and 8b are moved away from each other (in the right and left directions in the figure) so as not to prevent the deformation of the tube 2.

Figure 7D:
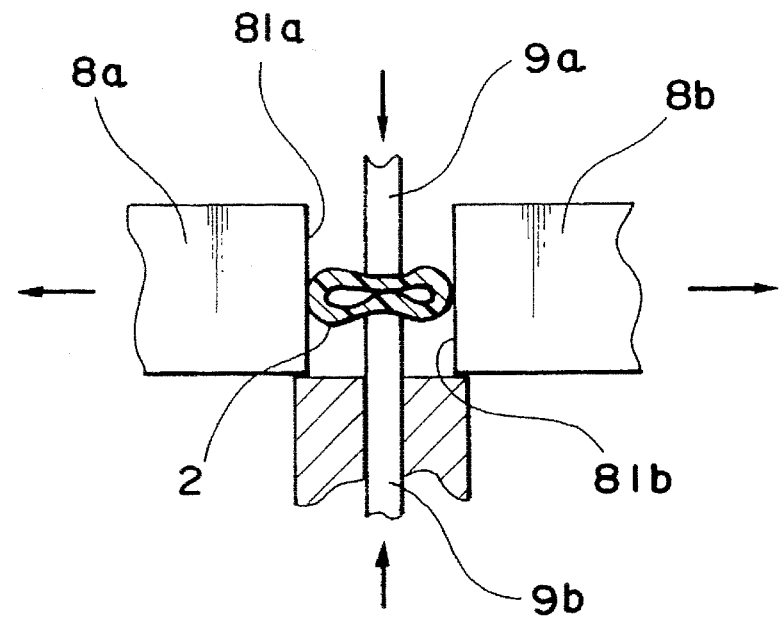
Figure 7E:
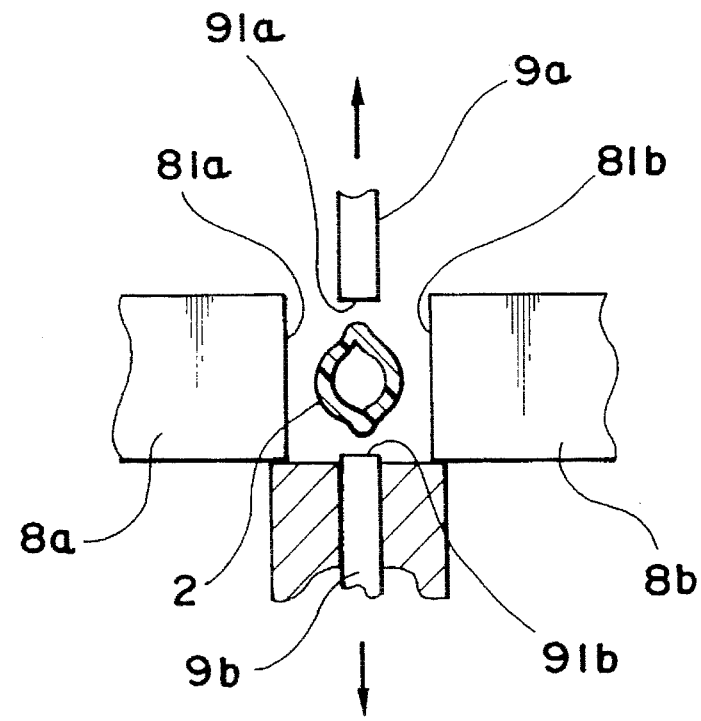

The second press members 9a and 9b are further moved in the vertical direction to crush the tube 2 perfectly, as shown in FIG. 7D, and thereafter the second press members 9a and 9b are returned to the original positions, as shown in FIG. 7E. In accordance with the above-mentioned operation, the deformed portion of the tube 2 can be also restored.

Figure 8A:
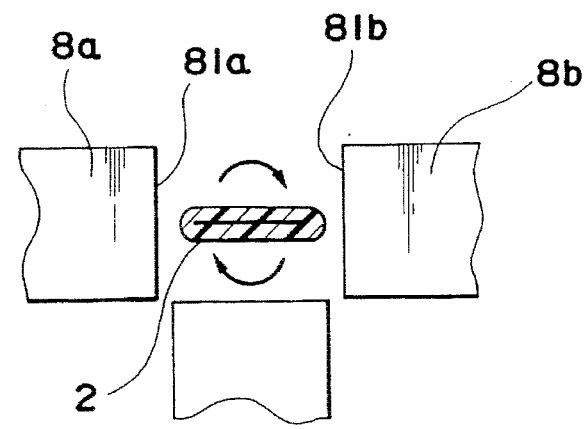
Figure 8B:
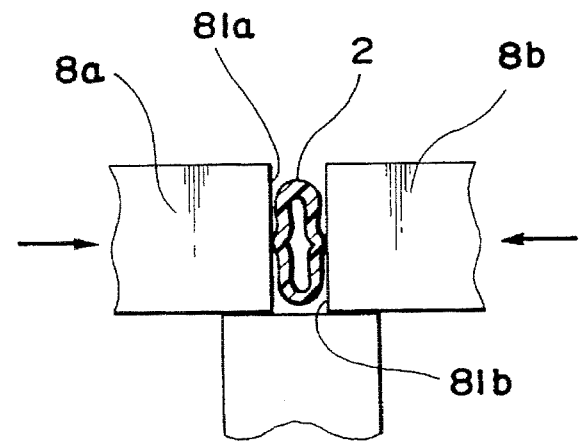
Figure 8C:
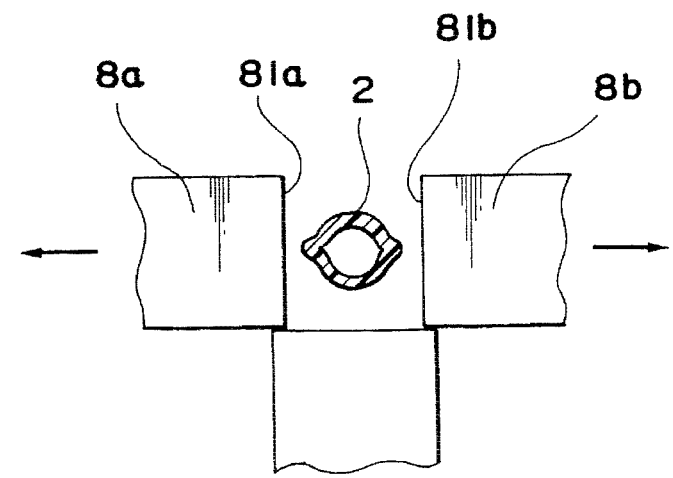

In the fifth embodiment, after the tube deformed portion is located between the press members 8a and 8b (see FIG. 7B), the press members 8a and 8b are returned to standby positions, respectively and further the tube 2 is rotated by 90 degrees, as shown in FIG. 8A. Under these conditions, the press members 8a and 8b are moved again to crush the tube 2, as shown in FIG. 8B. Thereafter, the press members 8a and 8b are returned to the standby positions again, respectively, as shown in FIG. 8C.

As the mechanism for rotating the tube 2 by 90 degrees, a pair of rollers for pinching the tube 2 (similar to the press rollers 3a and 3b of the first embodiment) can be used. When the two rollers are rotated in the same rotational direction, the tube 2 can be rotated.

In the above described embodiments, it should be noted that it is possible to constitute them in such a manner that only one of the press members can be moved.

As described above, the tube restoring apparatus according to the present invention can be utilized when the tubes are cut off or connected. These needs arise when liquid transfusing circuit is connected appropriately or various components of blood are separated from a blood collecting bag for reservation. In particular, the present invention is advantageous when the tubes are connected automatically.

Further, the tube restoring apparatus according to the present invention can be utilized to restore deformed portions of a tube which have been formed due to various causes other than the tube connection by the sterile tube connecting device.

Finally, it should be noted that the present invention is no limited to the above described embodiments. The scope of the present invention is defined only by the following claims.

What is claimed is:

1. A system for connecting two flexible tubes, comprising:
a tube connecting device for connecting by fusion a first flexible tube having an inner passage to a second flexible tube having an inner passage, the tube connecting device including a heated cutting element for cutting ends of the first and second tubes, the fusion of the first and second tubes producing a resulting tube having a deformed portion in which the inner passage is at least partially narrowed due to an at least partially fused inner surface of the resulting tube;
a tube restoring device for separating the fused inner surface of the resulting tube, said tube restoring device including a pair of press members which each have a press surface, said press members being spaced apart to define a space between the press surfaces through which the resulting tube passes, the tube restoring device including a moving device connected to at least one of the press members to move the at least one press member with the resulting tube positioned between the press surfaces to impart a compression force to the deformed portion of the resulting tube and thereby effect separation of the at least partially fused inner surface of the resulting tube; and a tube feed mechanism for advancing the first tube to a point at which a portion of the first tube is located at the tube connecting device and for advancing the resulting tube to position the deformed portion of the resulting tube between the press members.

2. The system according to claim 1, wherein at least one of the press members is provided with a notch located adjacent the press surface, said notch defining at least part of a tube insertion space for receiving the resulting tube.

3. The system according to claim 1, wherein said pressing members are rollers and said moving device moves the at least one pressing member in a rotational manner.

4. The system according to claim 1, wherein said pressing members are plates and said moving device moves the at least one pressing member in a linear manner.

* * * * *

UNITED STATES PATENT AND TRADEMARK OFFICE
CERTIFICATE OF CORRECTION

PATENT NO. : 5,554,253

DATED : September 10, 1996

INVENTOR(S) : Takahiko WATANABE

It is certified that error appears in the above-indentified patent and that said Letters Patent is hereby corrected as shown below:

In Column 10, line 20, after "tube" insert -- 2 --.

Signed and Sealed this

Eleventh Day of February, 1997

Attest:

BRUCE LEHMAN

Attesting Officer     Commissioner of Patents and Trademarks